United States Patent [19]

Blum

[11] Patent Number: 5,570,017
[45] Date of Patent: Oct. 29, 1996

[54] APPARATUS AND METHOD OF DAMAGE DETECTION FOR MAGNETICALLY PERMEABLE MEMBERS USING AN ALTERNATING MAGNETIC FIELD AND HALL EFFECT SENSORS

[75] Inventor: Dieter W. Blum, Delta, Canada

[73] Assignee: Canada Conveyor Belt Co., Inc., Surrey, Canada

[21] Appl. No.: 954,485

[22] Filed: Sep. 30, 1992

[51] Int. Cl.$^6$ ............................ G01N 27/72; G01R 33/12
[52] U.S. Cl. .......................... 324/232; 324/235; 324/238; 324/242
[58] Field of Search .................................. 324/226, 232, 324/237, 238, 239, 240, 241, 242, 243, 235

[56] References Cited

U.S. PATENT DOCUMENTS

| | | | |
|---|---|---|---|
| 4,427,940 | 1/1984 | Hirama et al. | 324/240 |
| 4,742,298 | 5/1988 | Ando et al. | 324/242 |
| 4,827,215 | 5/1989 | Vanderwolf | 324/232 |

*Primary Examiner*—Walter E. Snow
*Attorney, Agent, or Firm*—Robert B. Hughes

[57] ABSTRACT

An apparatus to detect anomalies in a member, such as a conveyor belt, having reinforcing cables therein made of a magnetically permeable material. There is coil means arranged to create a magnetic field as two longitudinally spaced first and second field components at longitudinally spaced locations. There are Hall effect sensors arranged to respond to modifications in each of the first and second field components. In a first embodiment, there is one set of sensors positioned between the first and second field components. In a second embodiment, there are two sets of sensors spaced at said first and second field components.

14 Claims, 5 Drawing Sheets

APPARATUS AND METHOD OF DAMAGE DETECTION FOR MAGNETICALLY PERMEABLE MEMBERS USING AN ALTERNATING MAGNETIC FIELD AND HALL EFFECT SENSORS

BACKGROUND OF THE INVENTION (a) Field of the Invention

The present invention relates to electromagnetic sensing and analysis of damage and/or deterioration of objects made of, or incorporating, a magnetically permeable material, and also to an apparatus and method for the analysis of data related to the same, and more particularly to such an apparatus and method which is particularly adapted to perform such sensing and analysis in an article such as an elongate conveyor belt, where reinforcing cables made of the magnetically permeable material are embedded in (and thus largely concealed in) a relatively non-permeable material such as the rubber like structure of the belt.

(b) Background Art

Large conveyor belts are used in a variety of applications, one of the major applications being in the mining industry where metal ore or other material is carried from the mine to a collecting location. For example, in an open pit mine, it is not uncommon to have a conveyor belt extending from a lower location upwardly for a distance as long as several thousand feet or even several miles. Such belts can possibly be as large as eight feet wide, and possibly as thick as four inches. The main belt material generally is a moderately flexible rubber-like material, and the belt is reinforced by a plurality of longitudinally extending metal cables which are positioned within the belt and extend along the length thereof.

One of the problems is that after continued use the metal reinforcing cables will deteriorate. For example, there may be a break in the conveyor belt material that would permit water or possibly even an acid (e.g. resulting from water reacting with the conveyed material) to come in contact with one or more of the cables to corrode the cables. The damage to the cables could come from an impact of some sort, or the deterioration could occur from natural wear or possibly fatigue of the metal because of long continued use. Sometimes the damage to the cable is a total break, and in some instances a partial deterioration that simply weakens the belt.

Since the metal cables in the belt are not visible, it is difficult to detect much of the damage to the cables. Unfortunately, when the damage is sufficiently severe so that it becomes outwardly visible, there may already have been a condition which would make further use of the belt dangerous. For this reason, it has usually been a practice in the industry to in a sense "overdesign" the belts so that there would be an adequately large margin of error to enable the belt to still function reasonably safely, even though there had been substantial degradation of the reinforcing cables.

Accordingly, an improved means of sensing deterioration (even a relatively small amount of deterioration) at an earlier time when it would not be visible by inspecting the outside of the belt would be advantageous.

SUMMARY OF THE INVENTION

The apparatus of the present invention is arranged to detect anomalies in a magnetically permeable member having a longitudinal axis, by providing a magnetic field at an operating area at which the magnetically permeable member is located. The apparatus is arranged relative to said member so that there can be movement of said member relative to said apparatus along the longitudinal axis.

The apparatus comprises coil means to generate the magnetic field as longitudinally spaced first and second field components at longitudinally spaced first and second locations at the operating area. There are sensing means arranged to respond to modifications in each of the first and second field components.

Thus, when a portion of the member having an anomaly passes through said first and second field location to create modifications in said first and second field components, the sensing means responds to modifications created by the anomaly in the first and second field components to detect the anomaly.

In the preferred form, the sensing means is arranged to respond to intensity of the magnetic field at a sensing location. In one embodiment, the sensing means is positioned between the field components so that the sensing location is between said field components. The field coil means is arranged to provide at least portions of the first and second field components both extending through the sensing locations. Also, in the preferred form, the sensing means is arranged to respond to shifts in balance between the first and second field components at the sensing location. More specifically, the coil means is arranged to provide first and second magnetic field loops which have adjacent portions thereof oriented oppositely to one another at the sensing location.

Also in the preferred form, the field coil means is arranged so that when there is substantially equal magnetic reluctance at the first and second field locations, the first and second field components substantially balance each other at the sensing area. When the magnetic reluctance at the first and second field locations is different, the first and second field components vary in strength to create net magnetic field portion at the sensing area. Thus, when the anomaly is at the first field location or at the second field location to cause differing magnetic reluctance in either said first or second field component, the magnetic field intensity at the sensing location is modified to cause the sensing means to respond.

The specific preferred configuration of the armature means is that the armature means comprises three longitudinally spaced armature portions, namely a forward armature portion, a rear armature portion and an intermediate armature portion between the forward and rear armature portions.

The coil means further comprises field coil generating means arranged to create the first field component as a magnetic loop extending through the forward armature portion and the intermediate armature portion, and to create the second field component as a second magnetic loop extending through the rear field component and through the intermediate armature portions. Portions of the forward and rear magnetic loops passing into said central armature portion are directed oppositely to one another.

The sensing means comprises a plurality of magnetic responsive sensors spaced from one another transversely to the longitudinal axis to extend transversely across the operating area. In the first embodiment, the sensors are positioned at a lower edge portion of the intermediate armature portion. As an alternative configuration, the sensors can be positioned at a location between upper and lower parts of the intermediate armature portion.

Alternating current power means is utilized to impose an alternating current on said field coil means to create said first and second field components as alternating magnetic fields.

The apparatus further comprises circuit means having receiving means to create a processing signal in response to an input from each of the sensors. The circuit further comprises multiplexing means to respond to each of said processing signals to create a plurality of multiplexer signal outputs corresponding to processing signals from the sensors.

Also, there is processing means to receive the multiplexer signal outputs to identify anomalies associated with certain of said sensors.

Also, the circuit means comprises field coil frequency control means responsive to linear speed of the member, relative to spacing of said first and second field components. This is done in a manner to relate frequency of the alternating field of said coil means to a time interval of one portion of the member moving, relative to said apparatus, from the first field location to the second field location.

In a second embodiment, the apparatus comprises first and second longitudinally spaced sensing means portions positioned at, respectively, the first and second field locations, respectively. Each of the first and second sensing portions is responsive to modifications in the first and second field components, respectively.

In the second embodiment, the field coil means is arranged so that when there is substantially equal. magnetic reluctance at the first and second field locations, the first and second field components are of substantially equal intensity, and when the magnetic reluctance at the first and second field locations is different, the first and second field components vary in strength. Thus, when the anomaly is at the first field location and then at the second field location to differing magnetic reluctance in said first and second field components, the magnetic field intensity at the sensing location is modified to cause said sensing means to respond.

In the preferred form, there is an armature means comprising three armature sections, as described above, and the first and second sensing portions are positioned between the forward armature portion and the intermediate armature portion and between the rear armature and intermediate armature portion, respectively.

Also, desirably alternating current power means is utilized to impose an alternating current on said coil means to create the first and second field components as alternating magnetic fields.

In the method of the present invention, an apparatus is utilized as described above. The magnetically permeable member is moved through the operating area to modify reluctance in the first and second components, with this being sensed by the sensing means.

Other features will become apparent from the following detailed description.

DESCRIPTION OF THE PREFERRED EMBODIMENT

Figure 1:
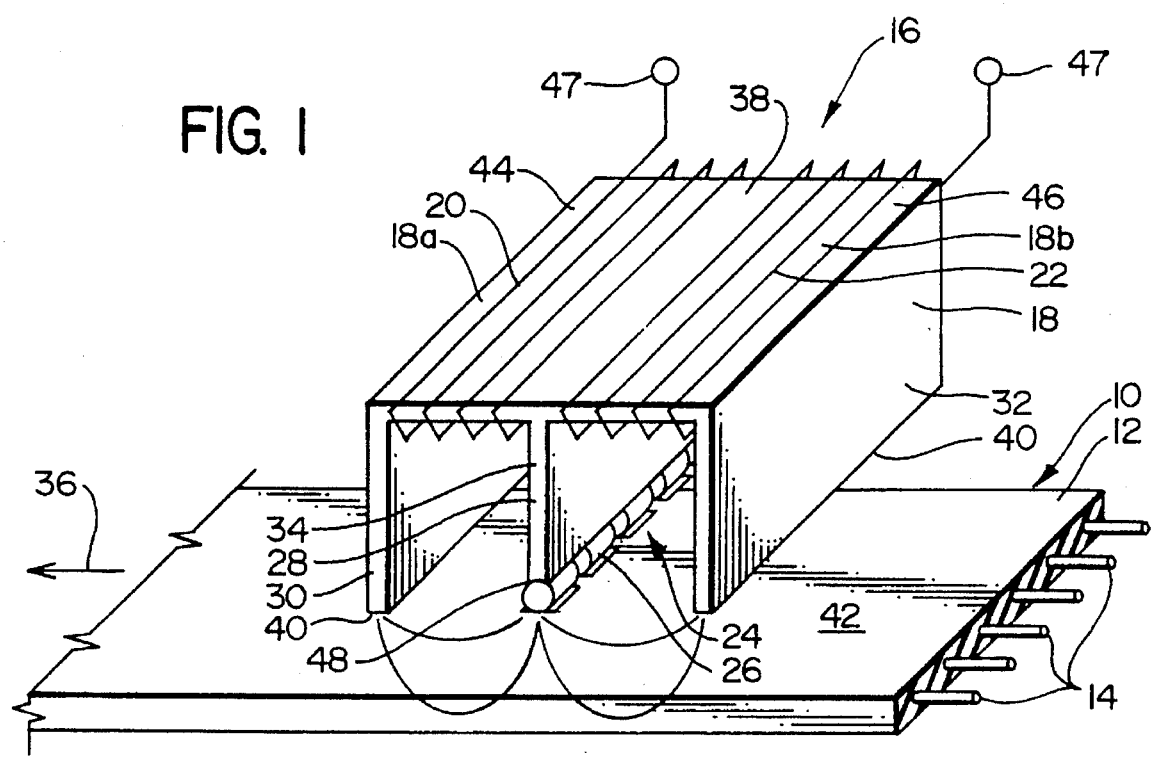
FIG. 1 is an isometric view of a first embodiment of the present invention illustrating the apparatus of the present invention in use in sensing possible defects in a conveyor belt.
Figure 2:
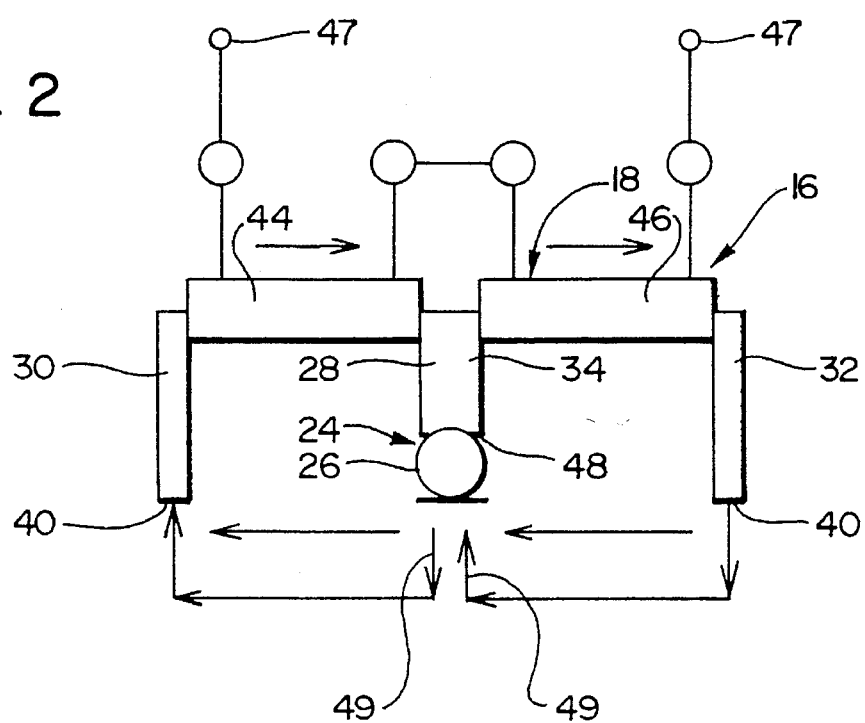
FIG. 2 is a side elevational view of the apparatus of FIG. 1, showing the conveyor belt in section.

With reference to FIGS. 1 and 2, there is shown a portion of a conveyor belt 10 having a main body portion 12 made of a rubber-like moderately resilient material that has relatively low magnetic permeability. Embedded in the interior of the main body portion 12 is a plurality of elongate longitudinally extending cables 14 which are spaced laterally from one another along substantially the entire width of the belt. Typically, in a belt having a width of between 12 to 96 inches and a vertical thickness dimension of between about ½ to 4 inches, there could be as many as 20 to 240 cables, spaced from one another at intervals from about 0.45 to 1.0 inch (measured center line to center line). The diameter of such cables could be, in a typical belt, from as large as ½ inch.

The apparatus of the present invention is generally designated 16, and it comprises a "W" shaped yoke 18, two field coils 20 and 22, respectively, wound around two portions 18a and 18b, respectively, of the yoke 18, and one set 24 of Hall effect sensors 26 positioned adjacent to the lower middle portion 28 of the yoke 18.

The yoke 18 is positioned immediately above the belt 10 and extends transversely across the entire width of the belt 10. The yoke 18 comprises three vertically aligned sections, namely forward and rear sections 30 and 32, respectively, and a middle section 34. (For purposes of description, the term "front" or "forward" will denote a direction in which the upper run of the belt 10 is moving, as indicated by the arrow 36, while the term "rear" or "rearward" denotes an opposite direction.

Also, the yoke 18 comprises a top horizontally aligned section 38 that is connected to (or made integrally with) the three vertically aligned sections 30–34. The lower edges 40 of the front and rear vertical sections 30 and 32 are spaced a short distance above (or possibly below the lower surface)the top surface 42 of the belt 10 (e.g. ¼ to 2 inches above). The yoke 18 was desirably made as a plurality of "W" shaped laminations (possibly ¼ of an inch in thickness) so as to reduce eddy currents in the yoke 18.

The two field coils 20 and 22 are wound around the forward and rear portions 44 and 46 of the top armature section 38, and these coils 20 and 22 are connected at 47 to a source of alternating current. Thus, it can be readily seen that the field coils 20 and 22 generate two alternating magnetic fields one of which extends in a loop from the forward section 30, through the front top yoke portion 44, through the middle yoke section 34 and thence through the portions of the cables 14 which are positioned between the yoke sections 30 and 34. The other alternating magnetic field extends through the rear section 34, through the adjacent portion 46 of the top yoke section, through the middle yoke section 34 and thence through the portions of the cables 14 that extend between the yoke sections 32 and 34.

The Hall effect sensors 26 extend in a transverse row at evenly spaced intervals across the width of the belt 10 and are spaced a short distance (typically between ¼ to 2 inch above the top surface 42 of the belt 10. The sensors 26 are positioned adjacent to, and immediately below the lower edge 48 of the middle section 34 of the yoke 18, and typically, these sensors 26 could be spaced laterally from one another about ¼ to ½ inch (measured center line to center line). Each Hall effect sensor 28 is aligned so that its active (i.e. magnetic flux sensing) axis will maximally intersect lines of flux extending upwardly into or downwardly from the lower edge 48 of the middle vertical section 34 above the yoke 18. The lower edge 48 of the middle yoke section 34 is located a short distance higher then the lower edges 40 of the front and rear sections 30 and 32. The set 24 of the Hall effect sensors 26 is mounted in some suitable manner, either directly to the armature 18 or possibly to some other mounting means. For example, the sensors 26 could be mounted to a related printed circuit board which may contain ancillary electronics. The supporting structure would support the entire armature 18, coils 20 and 22 and the sensor set 24 in a firm and rigid position that is in static proximity to the upper surface of the belt. For ease of illustration, the particular mounting device is not shown.

Since the magnetic lines of flux generated in the alternating field will seek the path of least reluctance, it can be seen that if the metal cables 14 are fully intact, these cables 14 would provide the path of least reluctance, and the lines of flux would be concentrated in the path provided by the portions of the cables 14 between the adjacent yoke sections (i.e. 30/34 and 32/34). On the other hand, if the cable portions between either of the yoke sections 30/34 or 32/34 are either broken or corroded so as to reduce their cross-sectional area, then there would be greater reluctance and thus there would a lesser concentration of the lines of flux in the adjacent section of cables 14.

As indicated previously, there is an alternating current that is directed through the field coils 20 and 22. The windings of these coils 20 and 22 are arranged so that the fields created by these two coils 20 and 22 are in the same direction at any one point in time. Thus, as illustrated in FIG. 2, during one half cycle of the alternating current, the direction of the magnetic fields created by the field coils 20 and 22 are both in a clockwise direction. On the other half cycle, the directions of the magnetic fields (as see in FIG. 2) will reverse and be counterclockwise.

To describe the effect of this on the operation of the present invention, let's consider a situation where the portions of the cables 14 and the belt 10 that are immediately below the front and rear portions of the yoke 18 are fully intact, similarly positioned in the belt, and of substantially uniform diameter. Thus, the reluctance provided by the two cable portions would be substantially identical.

By examining FIG. 2, it can be seen that with the two magnetic loops being oriented in the same direction (either both clockwise or both counterclockwise) the directions of the flux through the center vertical section 34 are actually opposite to one another. Thus, if the two portions of the cables 14 beneath the forward and rear portions of the yoke are both substantially intact and similarly placed so that these provide the same amount of reluctance, and with the fields created by the two windings (each having the same ampture turns) being of the same strength, the two magnetic loops will be of the same magnitude. Thus, the field portions that would exist in the vertical center section 34 of the yoke 18 essentially cancel each other out.

In this situation the magnetic field would extend through the two top sections 44 and 46, downwardly through the rear yoke section 32, then across the rear air gap to pass through the portions of the cords 14 that are beneath the yoke 18, thence upwardly through the forward air gap through the forward yoke section 30 to essentially close the loop. The two arrows indicated at 49 that would extend upwardly to or downwardly from the center yoke section 34 essentially do not exist. Also, there will be a rather small portion of the magnetic field which extends through the empty space immediately above the belt 10 and extending between the three yoke sections 30, 34 and 32, but this would be negligible.

Let us now take a situation where there is an anomaly in a certain portion of the cords or cables 14, either a break or possibly corrosion. This change in that portion of the cable or cables 14 would increase the reluctance to the magnetic field passing therethrough. When this portion of the belt having the anomaly is passing beneath the rear portion of the yoke 18 (i.e in the space between the rear section 30 and the middle section 34), the reluctance of that magnetic loop will increase, and thus the strength of the magnetic field that loops through the back portion of the yoke 18 will diminish. The net result is that the strength of the two magnetic loops will be out of balance (the forward magnetic loop having greater strength), so that there will be a net magnetic field reaching through either upwardly or downwardly through the middle section 34, depending upon the direction of the flow of current. (In FIG. 2, with the magnetic fields being counterclockwise, there would be a net downwardly directed magnetic field extending through the Hall effect sensor or sensors 26 and into the cables 14.) Thus, the Hall effect sensor or sensors 26 will detect this magnetic field and create a signal related thereto.

When the portion of the belt 10 having the damaged cables 14 passes immediately below the middle section 34, then the main portions of the cables 14 that are positioned rearwardly and forwardly of the middle section 34 of the yoke 18 would have substantially the same reluctance. Accordingly, the two magnetic loops would be balanced, and at that time the magnetic flux in the middle section 34 would effectively be zero, and the Hall effect sensor or sensors 26 would detect substantially no magnetic field.

Next, the anomaly in the cable or cables 14 would, as the belt 10 continues to travel forwardly, pass beneath the forward portion of the yoke 18, and the reluctance of the forward magnetic loop would decrease. This would again imbalance the two magnetic loops, with the rear magnetic loop being stronger, and this would in turn create magnetic lines of flux passing either upwardly or downwardly through the Hall effect sensor or sensors 26 in the area adjacent to the anomaly.

The signal or signals generated by the Hall effect sensor or sensors 26 create a "fingerprint" that would correspond to the nature of the anomaly. For example, if the anomaly is a sharp break in one or more of the cables, this would be expected to create a signal of possibly a shorter duration and having a distinctive shape. On the other hand, if the anomaly is corrosion that extends over a longer length of the cables 14 and the belt 10, then the anomaly would have a different fingerprint related to that anomaly.

As indicated previously, one possible source of error in using a Hall effect sensor in connection with a moving conveyor belt is that there may be some degree of flutter in the belt where the vertical location of the belt would change. Thus, if the belt 10 moves closer to the Hall effect sensors 26, this makes the air gaps shorter and would thus cause a change in the magnetic fields sensed by the Hall effect sensors 26.

This problem is alleviated as follows. One or more Hall effect sensors would be positioned adjacent to the belt 10, and these would be positioned and aligned so that they would respond to the fluctuating magnetic field created by the coils 20 and 22, somewhat in the manner disclosed in the second embodiment. As the belt 10 moves toward and away from the apparatus 16, the air gaps would increase or decrease, thus changing the amplitude of the magnetic field sensed by these particular Hall effect sensors. It can be assumed that the major length of the cables 14 of the conveyor belt 10 would be intact, and thus establish a "signature" that would represent a "healthy" portion of the belt moving toward and away from the apparatus 16. Thus, there would be provided a reference signal from which the other signals from the Hall effect sensors 26 could be compared, and the "footprint" of an anomaly could be analyzed, taking this factor into consideration.

Figure 3:
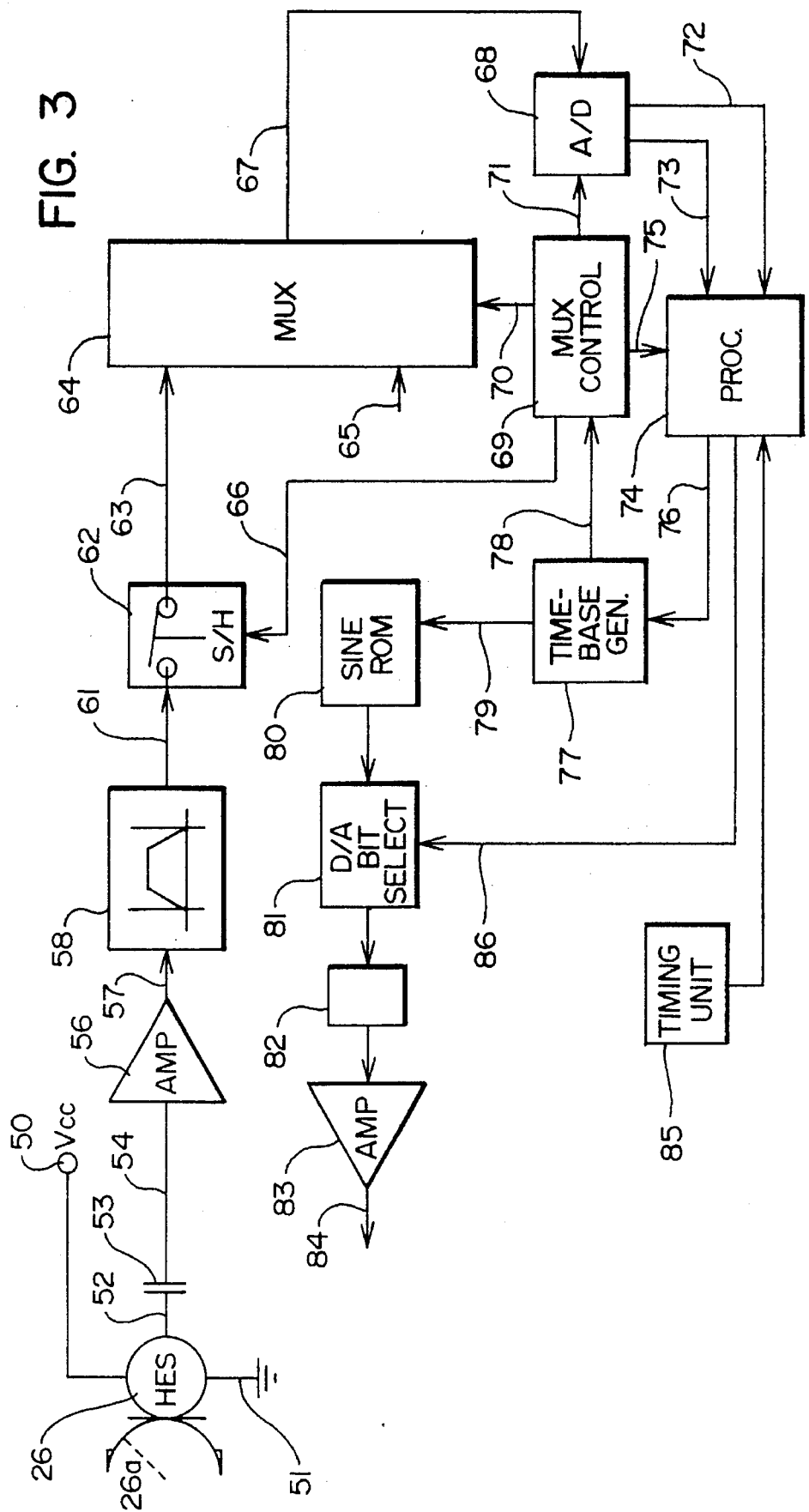
FIG. 3 is a schematic drawing illustrating the control circuitry and apparatus of the first embodiment of the present invention.

Reference is now made to FIG. 3 to describe the circuitry of the present invention. In FIG. 3, there is shown one Hall effect sensor 26 of the plurality of such sensors 26 in the Hall effect sensor set 24. As indicated previously, when there is an imbalance in the two magnetic loops in the yoke 18, this will create a fluctuating magnetic field adjacent to the lower edge 48 of the middle yoke section 18, and this will be detected by the sensor or sensors 26 at that location. Each Hall effect sensor 26 is connected to a positive voltage source at 50, and each sensor 28 has its GND terminal 51 connected to ground. The output terminal 52 is connected to respective coupling capacitors 53 which are in turn connected through a line 54 to the input terminal of a respective amplifier 56. These three aforementioned connections are generally representative of available Hall effect devices. The capacitors 53 serve to effectively block any DC component (i.e. offset) present in the output signals of the sensors 26.

The output from each differential amplifier 56 is directed through the line 57 to a related band pass filter 58 which excludes certain lower frequency and higher frequency signals. The lower frequency signals could occur, for example, from fluctuations in the up and down or sideways movement of the belt 10. The higher frequency signals could result from a variety of causes a related sample and hold unit 62.

It should be noted at this point that there is for each Hall effect sensor 26 a related capacitor 53, amplifier 56, band pass filter 58 and sample and hold unit 62. Therefore, each time there is a magnetic field 26a that is generated (in response to detecting an anomaly) to activate a related sensor or sensors 26, the signal from each sensor 26 passes through the capacitor 53, to be amplified by the related amplifier 56, through the band pass filter 58 to the related sample and hold unit 62.

The output from the sample and hold unit 62 is directed through a related line 63 to a multiplexer 64 which takes readings from all of the inputs (indicated at 65) from the various sample and hold units 62 sequentially so as to provide a single output 67.

The sample and hold units 62 each receive an input signal at 66 to tell that sample and hold unit 62 when to sample one of the signals from the band pass filter 58. The output of the sample and hold units are directed to the multiplexer 64, and the output of the multiplexer 64 is through a line 67 to an analog to digital converter 68. There is provided a multiplex control unit 69 which provides the sampling signal at 66 to each of the sample and hold units 62. Also, this multiplex control unit 69 sends a signal through line 70 to step the multiplexer 64. The analog to digital converter 68 sends a flag signal through the line 72 and sends its data output through the line 73 to the processor 74. The flag signal through the line 72 simply indicates to the processor 74 that data is being transmitted, with the actual transmission being sent through the line 73 (as indicated previously). The multiplexer control unit 69 also has an output through line 75 which supplies the processor 74 with information as to the channel from which a related Hall effect sensor 26 is being transmitted.

The processor 74 sends through the line 76 a signal to a time base generator 77 which in turn sends a timing signal through the line 78 to the multiplex control 69. In addition, the time base generator 77 through a line 79 sends a signal to the sine ROM 80 that translates the signal from the time base generator 77 into a digitally encoded sine wave and is transmitted through a digital to analog bit select 81 which produces a smooth since wave that passes through a low pass filter 82 and then to an amplifier 83. The output from the amplifier 83 is through the line 84, this being the current which drives the field coils 20 and 22 to in turn produce the magnetic fields in the yoke 18.

There is a timing unit 85 which is responsive to the speed of the conveyor 10, and sends a signal related to the conveyor speed to the processor 74. The processor 74 in turns sends a timing signal through the line 76 to the time base generator 77.

Further, the apparatus 16 can be provided with a temperature compensating feature. For example, a Hall effect sensor 26 can be provided at a location adjacent to the other Hall effect sensors 26, so as to be responsive to a magnetic field, and as the ambient temperature changes, this particular Hall effect sensor 26 would send a reference signal to the processor 74 so that the processor 74 could make a temperature compensation for the effect the temperature would have on the various sensors 26 that are responding to anomalies in the cables 14 in the belt 10.

When this anomaly passes under the rear portion of the yoke 18, the reluctance path through the rear loop changes (generally resulting in greater reluctance), and this will thus weaken the magnetic field of the rear loop. Thus, the forward and rear loops will be out of balance, and there will be a net flux in the central section 34 of the yoke 18. This will result in magnetic flux being directed either upwardly into the lower edge 40 of the central sections 34 or downwardly therefrom, and this will be detected by the Hall effect sensor 26. In like manner, as this anomaly passes under the forward section of the yoke 18, there will be an unbalanced where the forward loop is of lesser strength.

Thus, the only time the sensors 26 transmit a signal is when an anomaly is being detected.

As indicated previously, each Hall effect sensor 26 transmits its signal through a related capacitor 53, amplifier 56, and filter 58 to a related sample and hold unit 62. The outputs from the various sample and hold unit 62 is directed to the multiplexer 64.

To summarize the operation of the circuitry shown in FIG. 3, as indicated previously, the sensors 26 respond to a magnetic flux created by an anomaly created by an imbalance in the magnetic fields. Thus, when the cables 14 of the conveyor belt are undamaged, the permeability of each longitudinally spaced portion of the belt is substantially the same. The result is that there is substantially no magnetic field created at the location of the sensors 26, so that the sensors 26 do not produce an output signal.

However, let us take the situation where there is, for example, an anomaly in one or more the cables 14 in one localized section of the belt 10 (e.g. where possibly only one or two cables 14 are damaged at a particular location. The multiplexer 64 monitors the outputs 63 sequentially, with the stepping of the multiplexer 64 being controlled by the multiplexer control 69. Further, the multiplexer control 69 sends signals to the analog to digital computer 68. The data transmitted through the line 73 from the analog to digital computer 68 is received in the processor 74, and this data from the processor 74 can be either stored and/or displayed in some manner, or possibly be further processed to provide the desired format of the information. The processor 74 has additional functions, however. It receives the input from the timing unit 85, as to the speed of the belt 10. The processor 74 uses this information to send a signal to the time base generator 77, and the time base generator 77 in turn sends this information through the line to the multiplexer control 69. This information is necessary so that the multiplexer control 69 can time its actions in accordance with the linear speed of the belt 14.

Also the time based generator provides the signal to generate the sine waves through the sine ROM 80, digital to analog bits select 81, filter 82 and amplifier 83 to provide the execration current for the coils 20 and 22.

DESCRIPTION OF THE SECOND EMBODIMENT

Figure 4:
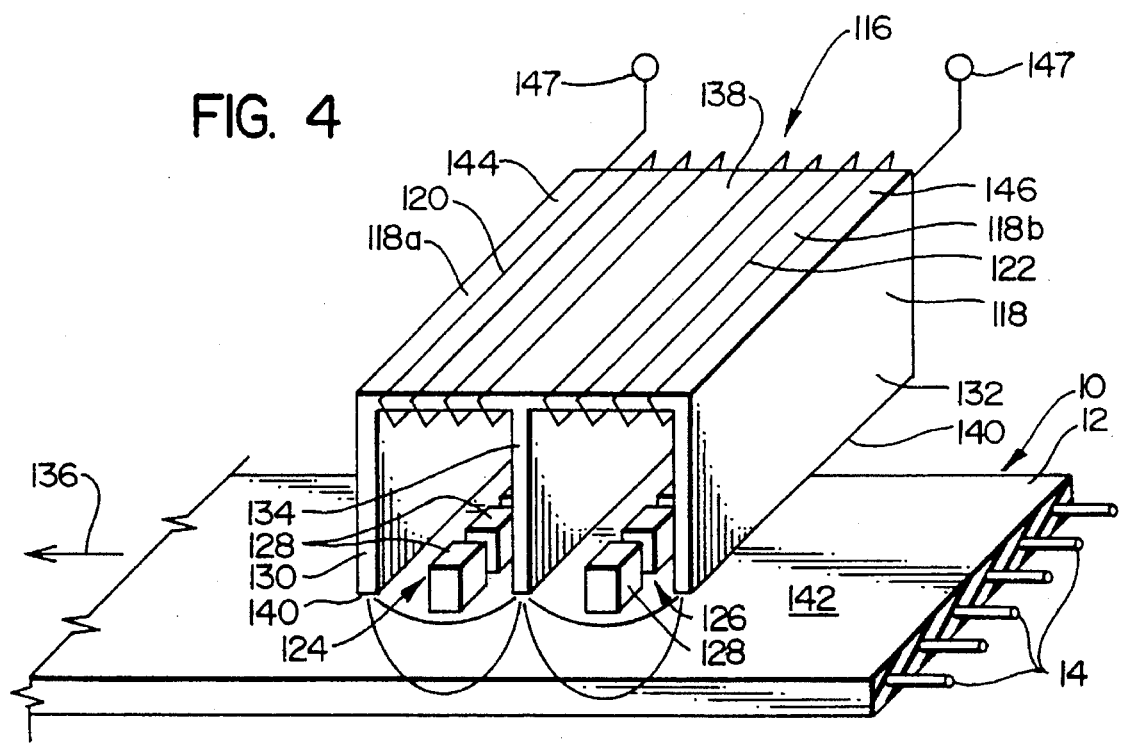
FIG. 4 is an isometric view similar to FIG. 1, showing a second embodiment of the present invention.
Figure 5:
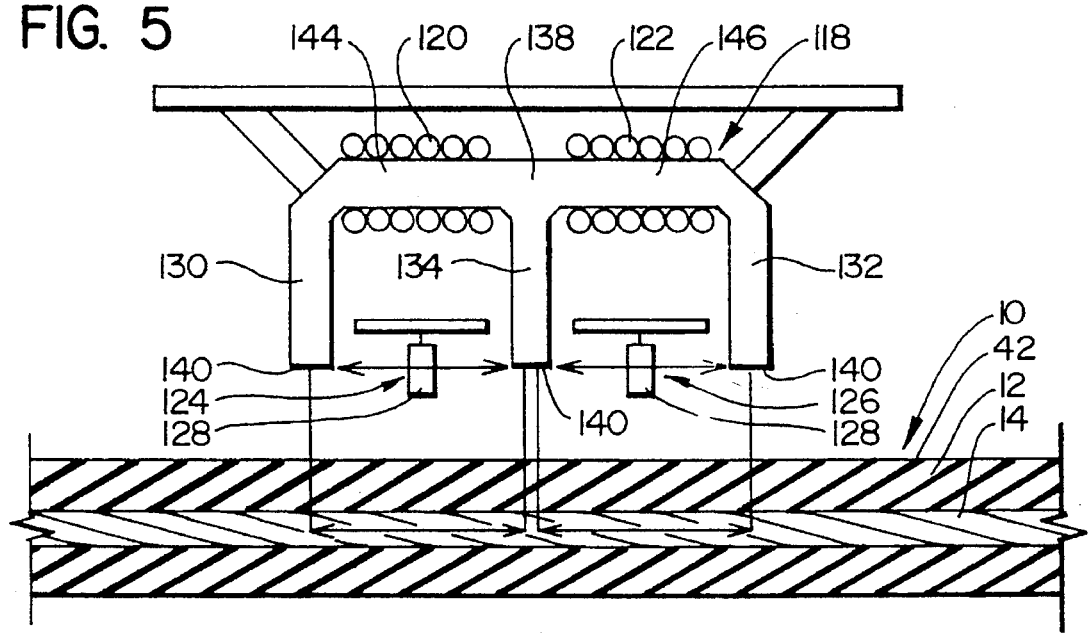
FIG. 5 is a side elevational view (similar to FIG. 2) of the second embodiment shown in FIG. 4.
Figure 6:
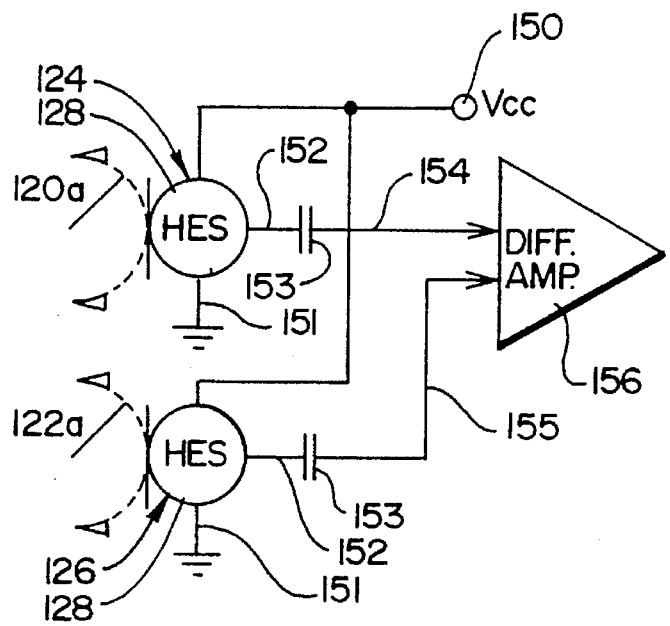
FIG. 6 is a schematic drawing illustrating the control circuitry and apparatus of the second embodiment shown in FIGS. 4 and 5.

The second embodiment of the present invention is shown in FIGS. 4, 5, and 6, where there is shown a portion of a conveyor belt 10 having a main body portion 12 made of a rubber-like moderately resilient material, as previously described.

The apparatus of the second embodiment is generally designated 116, and it comprises a "W" shaped yoke 118, two field coils 120 and 122, respectively, wound around two portions 118a and 118b, respectively, of the yoke 118, and two sets 124 and 126, respectively, of Hall effect sensors 28 positioned adjacent to the two yoke portions 18a and 18b.

The yoke 118 is positioned immediately above the belt 10 and extends transversely across the entire width of the belt 10. The yoke 118 comprises three vertically aligned sections, namely forward and rear sections 130 and 132 and a middle section 134. (For purposes of description, the term "front" or "forward" will denoted a direction in which the upper run of the belt 10 is moving, as indicated by the arrow 136, while the term "rear" or rearward" denotes an opposite direction.

Also, the yoke 118 comprises a top horizontally aligned section 138 that is connected to (or made integrally with) the three vertically aligned sections 130–134. The lower edges 140 of the three vertical sections 30–34 are spaced a short distance above the top surface 42 of the belt 10 (e.g. an inch or less).

The two field coils 120 and 122 are wound around the forward and rear portions 144 and 146 of the top armature section 138, and these coils 120 and 122 are connected at 144 to a source of alternating current. Thus, it can be readily seen that the field coils 120 and 122 generates two alternating magnetic fields one of which extends in a loop from the forward section 130, through the front top yoke portion 144, through the middle yoke section 134, and thence through the portions of the cables 14 which are positioned between the armature sections 130 and 134. The other alternating magnetic field extends through the rear section 134, through the adjacent portion 146 of the top armature section, through the middle armature section 134 and thence through the portions of the cables 14 that extend between the yoke sections 132 and 134.

The Hall effect sensors 128 of the forward set 124 extend in a transverse row at evenly spaced intervals across the width of the belt 10 and are spaced a short distance (typically between ¼ to 2 inch above the top surface 142 of the belt 10. The sensors 128 are positioned half way between the forward and intermediate armature sections 130 and 134, and typically, these sensors could be spaced laterally from one another about ¼ to ½ inch (measured center line to center line). Each Hall effect sensor 128 is aligned so that its active (i.e. magnetic flux sensing) axis will intersect lines of flux extending between the lower edges 140 of the vertical sections 130 and 134 above the belt 10. The sensors 128 of the rear set 126 are positioned between the rear yoke section 132 and the intermediate yoke section 134 in substantially the same manner as the Hall effect sensors 128 of the forward set 124. The two sets 124 and 126 of the Hall effect sensors 128 could be mounted to a related printed circuit board which may contain ancillary electronics. The supporting structure would support the entire armature 118, coils 120 and 122 and the sensor sets 124 and 126 in a firm and rigid position that is in static proximity to the upper surface of the belt. For ease of illustration, the particular mounting device is not shown.

Since the magnetic lines of flux generated in the alternating field will seek the path of least reluctance, it can be seen that if the metal cables 14 are fully intact, these cables 14 would provide the path of least reluctance, and the lines of flux would be concentrated in the path provided by the portions of the cables 14 between the two yoke sections (i.e. 130/134 and 132/134). On the other hand, if the cable portions between either of the yoke sections 130/134 or 132/134 are either broken or corroded so as to reduce their cross-sectional area, then there would be greater reluctance and thus there would be a lesser concentration of the lines of flux in the adjacent section of cables 14. Thus, if a particular Hall effect sensor 128 senses a stronger magnetic field, this would indicate that the adjacent path of reluctance through the adjacent cable or cables 14 would be greater, and thus indicate some form of damage. The output of each sensor 128 will be a function of the ampere turns product of the field coil 120 or 122, the sensitivity to the magnetic flux of the sensor 128 itself, the position of the sensor 128 in relation to the magnetic field lines, and the permeability of the reinforcing cables 14, and also the position of the adjacent portions of the cables 14 in relation to the magnetic field lines.

The operation of this second embodiment, relative to the sensing of the magnetic lines of flux differs from the first embodiment, and this will be described below.

The apparatus 116 is positioned above the belt 10 as shown in FIGS. 1 and 2 (and as described above), and the alternating current is imposed on the two windings or the two field coils 120 and 122. Then the conveyor belt 10 is set in motion so that it travels longitudinally beneath the apparatus 116. The Hall effect sensors 128 of the two sets 124 and 126 are monitored to sense any change in the strength of that portion of the magnetic field extending through the Hall effect sensors 128.

The output of each sensor 128 bears an inverse relationship to the permeability of the adjacent portions of the reinforcing cables 14 and to the position of the adjacent portions of the cables 14 in relation to the magnetic field lines. The magnitude of the output of the sensor 128 is a direct function of the strength of any intersecting magnetic flux (i.e. field lines). Therefore, as indicated above, the absence of any permeable material in the magnetic field generated by either of the coils 120 or 122 will appear as a strong flux (maximum field line intersection) and thereby produce the highest output. The presence of any permeable material will produce a path of lesser reluctance for the magnetic lines of force to follow and will thereby reduce the magnitude of the flux encountered by the Hall effect sensor 128, and correspondingly reduce the magnitude of its output.

As indicated previously, one potential source of error in using a Hall effect sensor in connection with a moving conveyor belt is that there may be some degree of flutter in the belt in that it may move up and down. Thus if the belt 10 moves closer to the Hall effect sensors 28, this makes the air gap shorter, and would thus cause a change in the magnetic field sensed by the Hall effect sensors 128. As will be described more fully hereinafter, this problem is alleviated in this second embodiment in that the outputs of two longitudinally lined sensors 128 of the sets 124 and 126 have their signals correlated to one another so as to eliminate the adverse effect of this belt flutter. This is done as follows.

The frequency of the energizing current in the yoke 118 is controlled, relative to the longitudinal spacing of the two Hall effect sensor sets 124 and 126 and also relative to the linear speed of the belt 10 so that the time interval of each sine wave is equal to the time it takes one portion of the belt 10 to travel from a location below one Hall effect sensor set 126 to the other Hall effect sensor 124. Thus, for example, let it be assumed that the belt is fluttering in a manner that it has moved upwardly a short distance and is more closely adjacent to the two sets of the Hall effect sensors 128. This would normally be expected to lessen the strength of the portion of the magnetic fields that pass through the two sets of Hall effect sensors 128. The sensing apparatus is able to compare the two sine wave portions imposed on that particular field coil 120 or 122 at the time that a given portion of the cable is beneath first the rear set 126 of sensors 128 and then under the forward set 124 of the sensors 128. If the amplitude of these two sine waves varies to the same degree, then this would indicate a condition where the belt 10 has moved either closer to or further away from the Hall effect sensors 128. The manner in which this is done will be described more fully later when the circuitry of the present invention is described relative to FIG. 6.

Let us assume that there are two locations on the belt 10 that are spaced longitudinally from one another a distance equal to the forward to rear spacing of the two sets 124 and 126 of Hall effect sensors 128. The alternating currents of the two windings 120 and 122 are in phase, and the frequency is controlled relative to the speed of travel of the belt 10 and the spacing of the Hall effect sensor sets 124 and 126. Thus, the two adjacent longitudinally spaced Hall effect sensors 128 from the forwards and rear sets 124 and 126 will be adjacent to the two spaced sections of the belt 10 at the same time. If the cables 14 at the two longitudinally spaced cable locations are undamaged, paths of the same reluctance are provided beneath the two longitudinally spaced Hall effect sensors 128, so that the sine waves sensed by the two adjacent longitudinal spaced Hall effect sensors 128 will increase or decrease in amplitude by the same amount, under circumstances where the belt has moved either closer to or away from the Hall effect sensors 128.

On the other hand, let us assume that there is an anomaly in one cable 14 at a location, and that there is a longitudinally spaced section spaced from this anomaly the same distance as the spacing of the two Hall effect sensor sets 124 and 126. Under these circumstances when the anomaly in the cable 14 is beneath a Hall effect sensor 128 of the rear set 126, the Hall effect sensor 128 of the rear set 126 will detect this anomaly, presumably by sensing an increase in the magnetic field passing through the Hall effect sensor 128 of the rear set 126 that is at that time adjacent to the anomaly. On the other hand, the adjacent forward Hall effect sensors 128 of the forward set 124 will be directly over an undamaged section of the cable 14 and its magnetic field will not be disturbed then a short increment of time later, this anomaly will have moved from eneath the rear Hall effect sensor set 126 to beneath the forward Hall effect sensor set 124, and at this time this anomaly will affect the pattern of the magnetic field in the forward yoke section 118a differently from an undamaged cable portion, and this will be detected in a Hall effect sensor of the forward set 124. As will be described later, the control circuitry of the prsent invention is able to distinguish that situation from that of which the change in the field strength is merely due to the flutter.

Also, as indicated previously, analysis has indicated that the "fingerprint" of the detected signal will vary, depending upon the type of anomaly which is being detected. For example, if there is a distinct break in the cable 14, the duration of time during which this break moves from beneath the rear sensor set 126 to the forward sensor sets is relatively short and the changes in the magnetic field could be two rather abrupt changes closer in time sequence. ON the other hand, let us assume that the anomaly is an extended area of corrosion which would pass between the two sensor sets 124 and 126 over a more extended interval of time. This wqould produce a significantly different fingerprint that would extend over a longer time interval. By analysing the configuration and duration fo the signal created by the anomaly, the nature of the anomaly can be more closely ascertained.

Reference is now made to FIG. 6 to describe the circuitry of the second embodiment of the present invention. The circuitry of the second embodiment is quite similar to that of the first embodiment, except in the manner in which the signals from the Hall effect sensor sets 124 and 126 are initially processed. The field prodsuced by the forward field coil is indicated at 120a, and that produced by the rear field coil is designated 122a. It can be seen that these magnetic fields 120a and 122a intersect the Hall effect sensors 128 of the forward and rear sets 124 and 126. Each Hall effect sensor 128 is, as in the first embodiment, connected to a positive voltage source at 150, and each sensor 128 has its GND terminat 152 connected to ground. The output terminals 152 are connected to respective coupling capacitors 153 which are in turn connected through lines 154 and 155 to the input terminals of a differential amplifier 156.

As in the first embodiment, there is a plurality of a differential amplifiers 156, each of which connects to respective band pass filters 158 so that each pair of a forward and rear sensor is connected to its related differential amplifier 156 and filter 158. It should be noted at this time that the variations in the two magnetic fields 120a and 120b would be in the form of two sine waves that are in phase with one another. The differential amplifier 156 detects a difference in these two sine waves. A difference in the two sine waves would ordinarily indicate some sort of an anomaly. On the other hand, if the sine waves change in amplitude simultaneously (due to the fluttering of the belt) this would not produce an output from the differential amplifiers 156. Thus (as described previously), the potential problem of the futter of the belt effecting the strength of the signals is alleviated, and the differential amplifier 156 generates a signal only when there is an anomaly, such as from damage to the cables 14 or a splkice in the cables 14.

The remainder of the circuitry for this embodiment is substantially the same as described in FIG. 3 with reference to the first embodiment. Accordingly, it is believed that no further description of this circuitry of the second embodiment is needed.

Figure 7:
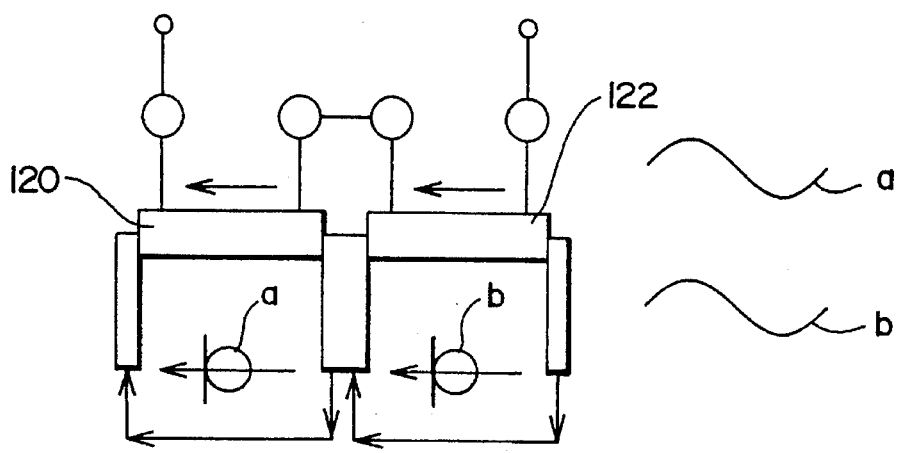
FIGS. 7 through 10 illustrate somewhat schematically four possible arrangements of the directions of the magnetic fields used in connection with the second embodiment.

In this second embodiment, there are at least four possible variations in the manner in which the oscillating magnetic fields are created, and these will be described with reference to FIGS. 7 through 10. In FIG. 7, there is illustrated an arrangement where the magnetic fields are in phase, and the directions of the two magnetic field created by the coils 120 and 122 are in the same direction. The orientation of the Hall effect sensors are the same, and the result in output signals are in phase. In this situation, the amplifier "a" is a differential amplifier to detect any differences in the signals generated by the two sets of Hall effect sensors.

Figure 8:
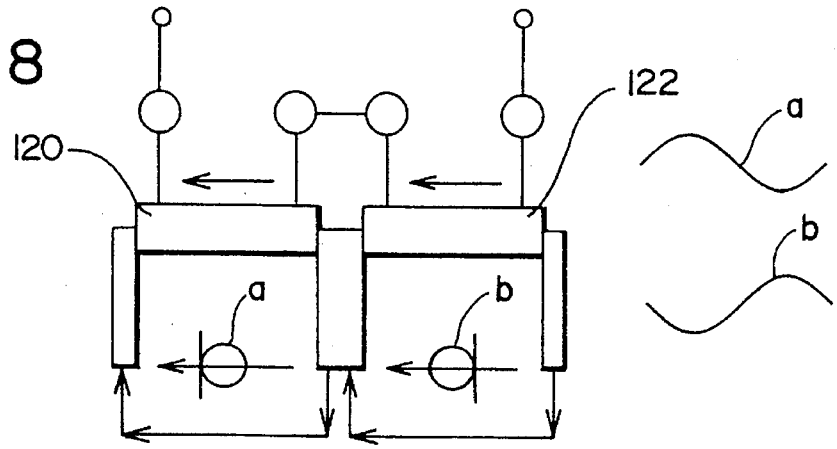

In FIG. 8, there is a second arrangement where the directions of the magnetic fields are the same, but the orientation of the Hall effect sensors is opposite, so that the resultant output signals from the Hall effect sensors are out of phase. In this instance, the signals, indicated at a and b at FIG. 8 are out of phase, and the amplifier 156, instead of being a differential amplifier would be a summing amplifier.

Figure 9:
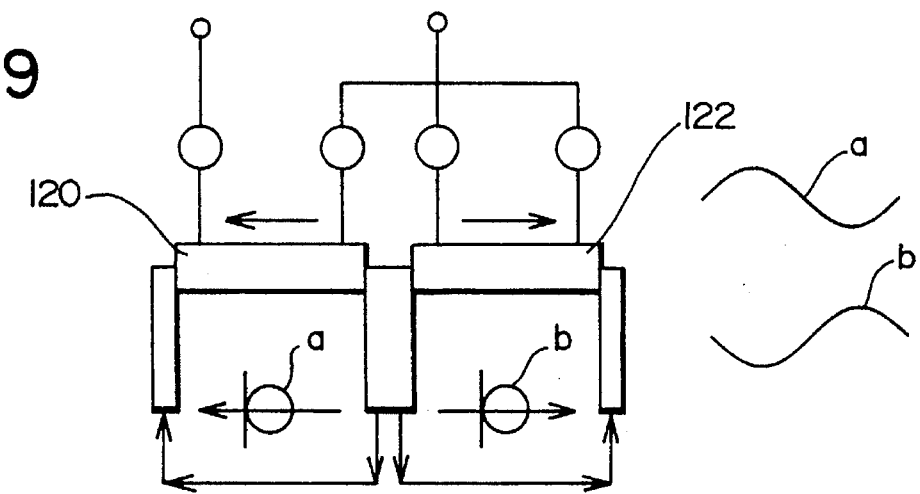

The third arrangement as shown in FIG. 9, where the magnetic fields are out of phase, but the orientation of the Hall effect sensors is the same. In this instance, as in the situation of FIG. 8, the resultant output signals of the Hall effect sensors are out of phase. Accordingly, the amplifier 156 would again be a summing amplifier.

Figure 10:
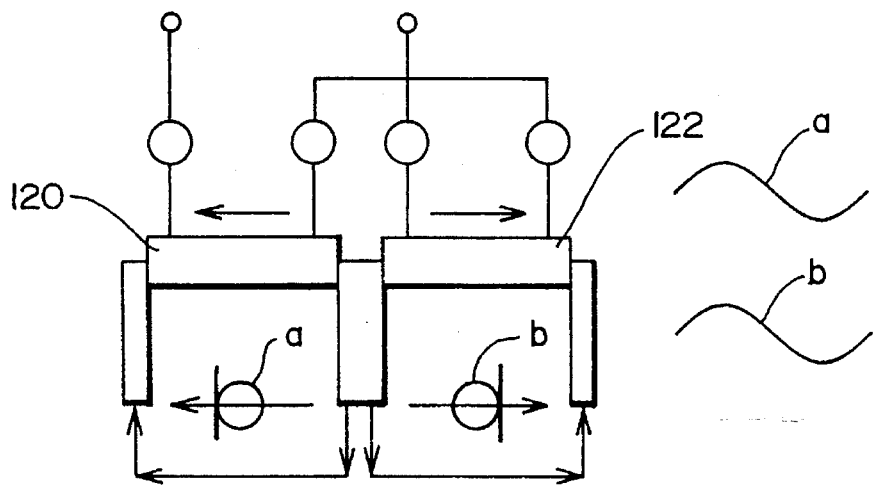

Finally, as shown in FIG. 10, the magnetic fields are out of phase, and there is an opposite orientation of the Hall effect sensors. The result is that the output signals are in phase, and as in FIG. 7, a differential amplifier 156 would be used.

It is to be recognized that various modifications can be made in the present invention without departing from the basic teachings thereof.

What is claimed:

1. An apparatus arranged to detect anomalies in a magnetically permeable member having a longitudinal axis, by providing a magnetic field at an operating area at which said magnetically permeable member is located, where said apparatus is arranged relative to said member so that there can be movement of said member relative to said apparatus along said longitudinal axis, said apparatus comprising:
   a. coil means to generate said magnetic field as an alternating magnetic and at longitudinally spaced first and second field components at longitudinally spaced first and second field locations at said operating area;
   b. sensing means arranged to respond to modifications of said first and second field components, said sensing means being arranged to respond to differences in field intensity of said first and second field components at a sensing location, whereby when a portion of said member having an anomaly passes through said first and second field locations to create modifications in said first and second field components, said sensing means responds to modifications created by said anomaly in said first and second field components to detect said anomaly;
   c. said sensing means comprising a plurality of sensors, said apparatus further comprising circuit means having receiving means to create a processing signal in response to an input from each of said sensors, said circuit means further comprising multiplexing means to respond to each of said processing signals to create a plurality of multiplexer signal outputs corresponding to processing signals from the sensors, and processing means to receive said multiplexer signal outputs to identify anomalies associated with certain of said sensors;
   d. field coil frequency control means responsive to linear speed of said member, relative to spacing of said first and second field components, in a manner to relate frequency of the alternating field of said coil means to a time interval of one portion of said member moving, relative to said apparatus, from the first field location to the second field location.

2. A method to detect anomalies in a magnetically permeable member having a longitudinal axis comprising:
   a. providing a magnetic field at an operating area at which said magnetically permeable member is located, and arranging said apparatus relative to said member so that there is movement of said member relative to said apparatus along said longitudinal axis;
   b. providing coil means to generate said magnetic field as longitudinally spaced first and second field components at longitudinally spaced first and second field locations at said operating area;
   c. utilizing sensing means to respond to modifications in each of said first and second field components, in a manner that when a portion of said member having an anomaly passes through said first and second field locations to create modifications in said first and second field components, said sensing means responds to modifications created by said anomaly in said first and second field components to detect said anomaly;
   d. utilizing field coil frequency control means responsive to linear speed of said member, relative to spacing of said first and second field components, in a manner to relate frequency of the alternating field of said coil means to a time interval of one portion of said member moving, relative to said apparatus, from the first field location to the second field location.

3. The method as recited in claim 2 further comprising utilizing field coil frequency control means responsive to linear speed of said member, relative to spacing of said first and second field components, in a manner to relate frequency of the alternating field of said coil means to a time interval of one portion of said member moving, relative to said apparatus, from the first field location to the second field location.

4. An apparatus arranged to detect anomalies in a magnetically permeable member having a longitudinal axis, by providing a magnetic field at an operating area at which said magnetically permeable member is located, where said apparatus is arranged relative to said member so that there can be movement of said member relative to said apparatus along said longitudinal axis, said apparatus comprising:
   a. coil means to generate said magnetic field as an alternating magnetic field and as longitudinally spaced first and second field components at longitudinally spaced first and second field locations at said operating area;
   b. absolute field intensity sensing means arranged to respond to modifications of said first and second field components, whereby when a portion of said member having an anomaly passes through said first and second field locations to create modifications in said first and second field components, said sensing means responds to modifications created by said anomaly in said first and second field components to detect said anomaly;

c. field coil frequency control means responsive to linear speed of said member, relative to spacing of said first and second field components, in a manner to relate frequency of the alternating field of said coil means to a time interval of one portion of said member moving, relative to said apparatus, from the first field location to the second field location.

5. A method of detecting faults in a plurality of magnetically permeable reinforcing cable members of a conveyor belt, where said belt comprises a main body portion having upper and lower surfaces, a longitudinal axis, a transverse axis, and a vertical axis, and said reinforcing members are longitudinally aligned and positioned within the main body portion at spaced intervals along the transverse axis of the belt, said method comprising:

a. positioning magnetic field means comprising forward, rear and middle armature portions to provide a longitudinally aligned magnetic field at an operating location adjacent to one of the surfaces of the belt;

b. causing relative movement of said belt and said magnetic field means in a manner that said belt moves longitudinally and forwardly relative to said magnetic field means so that the cable members are passing through the magnetic field;

c. providing said magnetic field means with a first forward field component and a second rear field component, with said first and second field components being longitudinally spaced and longitudinally aligned, with said forward field component extending from the forward armature Portion through, and proximate to, adjacent forward portions of the cable members to the middle armature portion, and with said rear field component extending from the rear armature portion through, and proximate to, adjacent rear portions of the cable members to the middle armature portion, said first and second magnetic field components being arranged so that at any one time, the first and second magnetic field components are aligned and in the same longitudinal direction, said magnetic field means being positioned and arranged so that with the armature portions similarly spaced and positioned relative to the belt, and with the forward and rear cable portions having substantially equal reluctance paths relative to the first and second field components, flux fields of the first and second field components passing through the first and second cable portions and adjacent thereto are substantially similar and of equal intensity and in the same direction, and with the reluctance paths of the forward and rear adjacent cable portions having different reluctance paths, the magnetic flux field portions of the first and second field components through the first and second cable portions differ from one another and the magnetic flux field portions of the first and second field components adjacent to and outside of the belts, and also spaced away from the cables within the belt the belt differ from one another;

d. providing a plurality of sensors capable of responding to absolute field strength, regardless of variations in field strengths, and positioning these sensors at transversely spaced locations in said magnetic field adjacent to said conveyor belt to respond to differences in absolute field strength of first and second field portions of said first and second field components at a location outside of the belt and spaced from the cables;

e. monitoring each of said sensors to respond to relative absolute field strengths of said first and second portions of said first and second field components to detect a situation where a cable fault passing from a location of said first armature portion to said middle armature portion causes a change in flux field intensity of said first field portion, and said cable fault passing from said middle armature portion to said rear armature portion causes a change in flux field intensity of said second field portion, by detecting an imbalance between field intensities of said first and second field portions;

whereby said imbalance of said first and second field components can be detected, even during periods when there is no variations in field intensity of said first and second field components, and when said belt is moving toward and away from said sensor.

6. The method as recited in claim 5 wherein said sensors are positioned between said field components and adjacent to said middle armature portion so that said first and second field components both extend through the sensors.

7. The method as recited in claim 5 herein said sensors are positioned at a lower edge portion of said middle armature portion.

8. The method as recited in claim 5 further creating a processing signal in response to an input from each of said sensors, utilizing multiplexing means to respond to each of said processing signals to create a plurality of multiplexer signal outputs corresponding to processing signals from the sensors, and receiving said multiplexer signal outputs to identify anomalies associated with certain of said sensors.

9. The method as recited in claim 5 further comprising providing said sensors as first and second longitudinally spaced sets of sensors positioned respectively, between said front and middle armature portions and said middle and rear armature portions, respectively.

10. An apparatus to detect faults in a plurality of magnetically permeable reinforcing cable members of a conveyor belt, where said belt comprises a main body portion having upper and lower surfaces, a longitudinal axis, a transverse axis, and a vertical axis, and said reinforcing members are longitudinally aligned and positioned with the main body portion at spaced intervals along the transverse axis of the belt, said method comprising:

a. magnetic field means comprising forward, rear and middle armature portions to provide a longitudinally aligned magnetic field at an operating location adjacent to one of the surfaces of the belt;

b. mounting means to position said magnetic field means so that with relative movement of said belt and said magnetic field means in a manner that said belt moves longitudinally and forwardly relative to said magnetic field means, the cable members are passing through the magnetic field;

c. said magnetic field means being arranged to provide a first forward field component and a second rear field components, with said first and second field components being longitudinally spaced and longitudinally aligned, with said forward field component extending from the forward armature portion through, and proximate to, adjacent forward portions of the cable members to the middle armature portion, and with said rear field components extending from the rear armature Portion through, and proximate to, adjacent rear portions of the cable members to the middle armature portion, said first and second magnetic field components being arranged so that at any one time, the first and second magnetic field components are aligned and in the same longitudinal direction, said magnetic field means being positioned and arranged so that with the armatures similarly spaced and positioned relative to the belt, and with the forward and rear cable portions having substantially equal reluctance paths relative to the first and second field components, flux fields of the first and second field components passing through the first and second cable portions and adjacent thereto are substantially similar and of equal intensity and in the same direction, and with the reluctance paths of the forward and rear adjacent cable portions having different reluctance paths, the magnetic flux field portions of the first and second field components through the first and second cable portions differ from one another and the magnetic flux field portions of the first and second field components adjacent to and outside of the belts, and also spaced away from the cables within the belt, differ from one another;

d. a plurality of sensors capable of responding to absolute field strength, regardless of variations in field strengths, positioned at transversely spaced locations in said magnetic field adjacent to said conveyor belt to respond to differences in absolute field strength of first and second field portions of said first and second field components at a location outside of said belt and spaced from the cables;

e. monitoring means to monitor each of said sensors to respond to relative absolute field strengths of said first and second field portions to detect a situation where a cable fault passing from a location of said first armature portion to said middle armature causes a change in flux field intensity of said first field portion, and said cable fault passing from said middle armature portion to said rear armature portion cause a change in flux field intensity of said second field portion, by detecting an imbalance between field intensities of said first and second field portions:

whereby an imbalance of said first and second field components can be detected, even during periods when there is no variation in field intensity of said first and second field components and when said belt is moving toward and away from said sensors.

11. The apparatus as recited in claim 10, wherein said sensors are positioned between said field components and adjacent to said middle armature portion so that said first and second field components both extend through the sensors.

12. The apparatus as recited in claim 10, wherein said sensors are positioned at a lower edge portion of said middle armature portion.

13. The apparatus as recited in claim 10, wherein there is multiplexing means to respond to signals from each of said sensors to create a plurality of multiplexer signal outputs corresponding to signals from the sensors, to identify anomalies associated with certain of said sensors.

14. The apparatus as recited in claim 10, wherein there is first and second longitudinally spaced sets of sensors positioned respectively, between said front and middle armature portions and said middle and rear armature portions, respectively.

* * * * *